US012611265B2

(12) United States Patent
Franklin et al.

(10) Patent No.: US 12,611,265 B2
(45) Date of Patent: Apr. 28, 2026

(54) MEDICAL DEVICE PROJECTION SYSTEM

(71) Applicant: C. R. Bard, Inc., Franklin Lakes, NJ (US)

(72) Inventors: Jeff E. Franklin, Hamilton, OH (US); Paul Thomas Mannion, Eliot, ME (US); Alex Ivlev, Milcreek, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 105 days.

(21) Appl. No.: 18/281,448

(22) PCT Filed: Mar. 25, 2022

(86) PCT No.: PCT/US2022/021936
§ 371 (c)(1),
(2) Date: Sep. 11, 2023

(87) PCT Pub. No.: WO2022/204506
PCT Pub. Date: Sep. 29, 2022

(65) Prior Publication Data
US 2024/0164852 A1      May 23, 2024

Related U.S. Application Data

(60) Provisional application No. 63/166,825, filed on Mar. 26, 2021.

(51) Int. Cl.
*A61B 34/00*        (2016.01)
*A61B 18/20*        (2006.01)
(Continued)

(52) U.S. Cl.
CPC .............. *A61B 34/25* (2016.02); *A61B 18/20* (2013.01); *A61B 46/23* (2016.02); *A61B 90/36* (2016.02);
(Continued)

(58) Field of Classification Search
CPC .............. A61B 34/25; A61B 2034/252; A61B 2034/254; A61B 2034/256;
(Continued)

(56) References Cited

U.S. PATENT DOCUMENTS

2009/0294339 A1* 12/2009 Biewer ................... A61M 1/28
                                                          210/85
2014/0280474 A1*  9/2014 Lynn ...................... G16H 40/67
                                                          709/203
(Continued)

FOREIGN PATENT DOCUMENTS

WO        2016133644 A1      8/2016
WO        2018226850 A1      12/2018
(Continued)

OTHER PUBLICATIONS

PCT/US2022/021936 filed Mar. 25, 2022, International Search Report and Written Opinion dated Sep. 7, 2022.

*Primary Examiner* — Robert A Lynch
(74) *Attorney, Agent, or Firm* — Rutan & Tucker LLP

(57)              ABSTRACT

Disclosed herein is a medical device projection system. The medical device projection system includes a first medical device outside of a sterile field, the first medical device having a user control interface including a plurality of parameters. The medical device projection system further includes a projector within the sterile field, the projector in communication with the first medical device and configured to project a mixed reality visual representation of the user control interface on a surface.

27 Claims, 7 Drawing Sheets

(51) Int. Cl.
      *A61B 46/23*       (2016.01)
      *A61B 90/00*       (2016.01)
(52) U.S. Cl.
      CPC . *A61B 2090/365* (2016.02); *A61B 2560/0487*
                                                         (2013.01)
(58) Field of Classification Search
      CPC ... A61B 2034/258; A61B 46/00; A61B 46/20;
            A61B 46/23; A61B 90/36; A61B 90/361;
            A61B 90/37; A61B 2090/365; A61B
            2090/366; A61B 2090/371; A61B
            2090/372; A61B 2090/373; A61B 18/20;
            A61B 18/203; A61B 2018/2015; A61B
            2018/202; A61B 2018/2023; A61B
            2018/2035; A61B 2018/20351; A61B
            2018/20353; A61B 2018/20355; A61B
            2560/0487; G16H 40/63; G16H 40/67;
            G06F 3/017; G06F 3/0482; G06F
            3/04842; G06F 3/04847; H04L 67/10
      See application file for complete search history.

(56)                References Cited

U.S. PATENT DOCUMENTS

| | | | |
|---|---|---|---|
| 2015/0187196 A1* | 7/2015 | Blair ..................... | G16H 40/63 |
| | | | 340/691.6 |
| 2016/0180046 A1* | 6/2016 | Sezeur ................. | G06F 3/0482 |
| | | | 700/90 |
| 2017/0312035 A1* | 11/2017 | May ...................... | A61B 50/33 |
| 2019/0012944 A1* | 1/2019 | Hall ...................... | A61B 34/25 |
| 2019/0125454 A1 | 5/2019 | Stokes et al. | |
| 2020/0400930 A1* | 12/2020 | D'Costa ................ | G16H 10/40 |

FOREIGN PATENT DOCUMENTS

| | | | | |
|---|---|---|---|---|
| WO | WO-2019074755 A1 * | 4/2019 | ............ | A61B 18/20 |
| WO | 2019236505 A1 | 12/2019 | | |
| WO | 2022204506 A1 | 9/2022 | | |

* cited by examiner

*200*

PLACING A PROJECTOR IN COMMUNICATION
WITH A FIRST MEDICAL DEVICE
*202*

PLACING THE PROJECTOR IN A STERILE FIELD
*204*

PROJECTING A MIXED REALITY VISUAL
REPRESENTATION OF THE USER CONTROL
INTERFACE ON A SURFACE
*206*

PROVIDING ONE OR MORE PARAMETER
CHANGES TO THE FIRST MEDICAL DEVICE
*208*

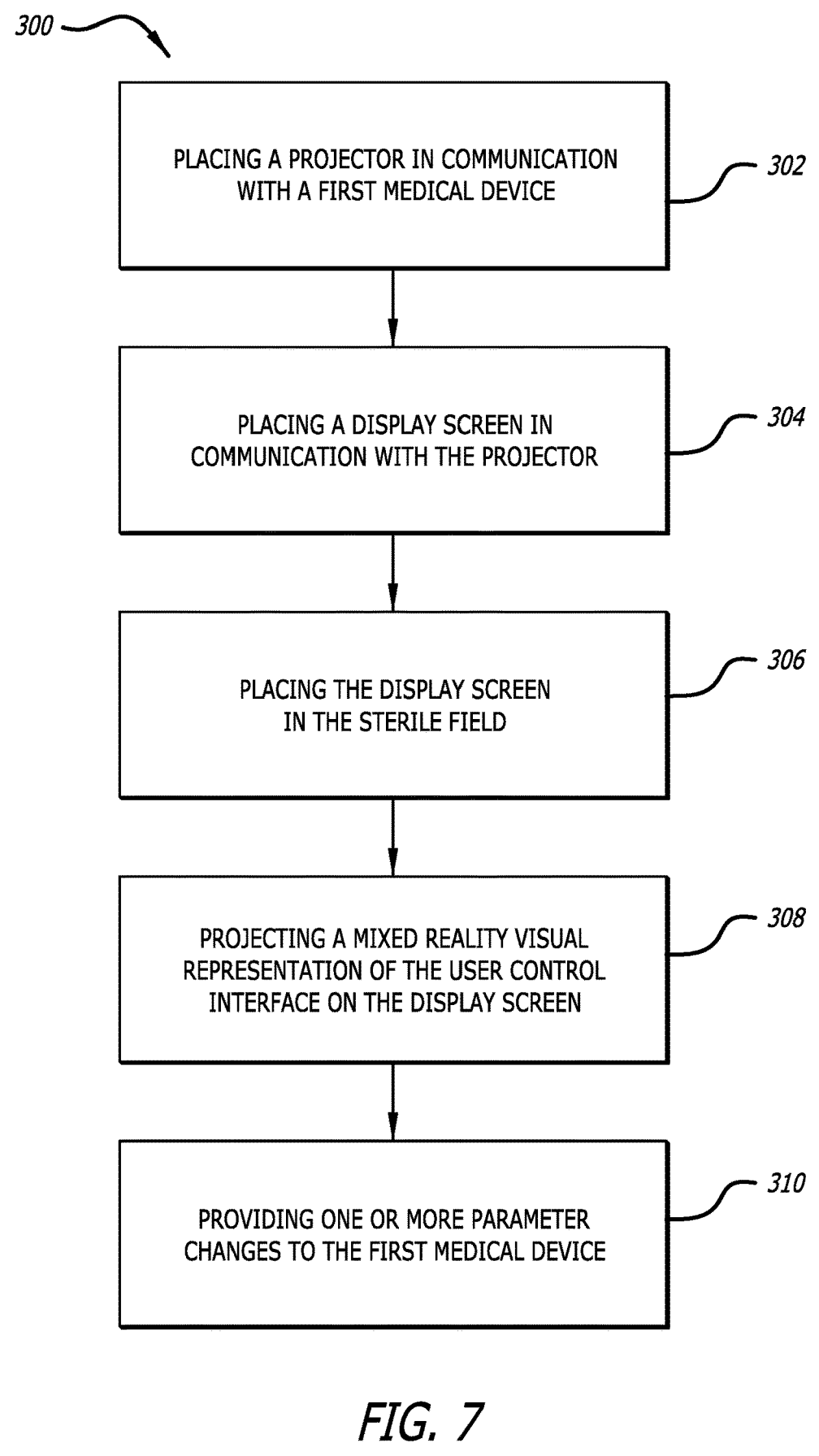

300

PLACING A PROJECTOR IN COMMUNICATION WITH A FIRST MEDICAL DEVICE — 302

PLACING A DISPLAY SCREEN IN COMMUNICATION WITH THE PROJECTOR — 304

PLACING THE DISPLAY SCREEN IN THE STERILE FIELD — 306

PROJECTING A MIXED REALITY VISUAL REPRESENTATION OF THE USER CONTROL INTERFACE ON THE DISPLAY SCREEN — 308

PROVIDING ONE OR MORE PARAMETER CHANGES TO THE FIRST MEDICAL DEVICE — 310

FIG. 7

MEDICAL DEVICE PROJECTION SYSTEM

PRIORITY

This application is a U.S. national stage application of International Application No. PCT/US2022/021936, filed Mar. 25, 2022, which claims the benefit of priority to U.S. Provisional Application No. 63/166,825, filed Mar. 26, 2021, each of which is incorporated by reference in its entirety into this application.

BACKGROUND

When a sterile field is present during a medical procedure, it can be difficult for a clinician to interact with, provide input to or change parameters on a medical device used in the procedure when the medical device is located outside of the sterile field. The clinician must exit the sterile field or relay the clinician's input to a person outside of the sterile field. This process can take time away from the procedure and require reagents for sterilization of the clinician each time the clinician exits the sterile field. It would be beneficial to the clinician be able to interact with, provide input to or change parameters on the medical device while maintain sterility within the sterile field. Disclosed herein is a medical device projection system and a method that address the foregoing.

SUMMARY

Disclosed herein is a medical device projection system including a first medical device and a projector. The first medical device is configured to be outside of a sterile field and the first medical device includes a user control interface including a plurality of parameters. The projector is configured to be within the sterile field, and is in communication with the first medical device and is configured to project a mixed reality visual representation of the user control interface on a surface.

In some embodiments, the surface is visible to a user and is inside the sterile field or outside the sterile field.

In some embodiments, the surface includes a floor, a ceiling, a surface of a second medical device, or a sterile drape.

In some embodiments, the projector includes one or more buttons configured to control the plurality of parameters, the one or more buttons being coupled to a left side, a right side, or a back side of a projector body.

In some embodiments, the one or more buttons include a clickable scroll wheel.

In some embodiments, the projector includes a projector body coupled to a projector stand, the projector stand coupled to a right side or a left side of the projector body.

In some embodiments, the projector stand includes a projector stand base or two or more projector stand legs.

In some embodiments, the projector is configured to rotate annularly around a projector stand axis.

In some embodiments, the projector includes a console having an energy source, one or more processors, non-transitory computer readable medium and a plurality of logic modules.

In some embodiments, the plurality of logic modules, when executed by the processor, are configured to perform operations including receiving a depiction of the user control interface from the first medical device, correlating the status of the one or more buttons with one or more parameter changes on the user control interface, projecting a mixed reality visual representation of the user control interface, including any parameter changes on a surface, and transmitting the one or more parameter changes from the projector to the first medical device.

In some embodiments, the first medical device includes a laser and the plurality of parameters include laser pulse energy, laser frequency, and laser pulse duration.

In some embodiments, the projector is configured to be sterile or placed into a sterile bag.

Also disclosed is a medical device projection system including a first medical device, a projector, and a display screen. The first medical device is configured to be outside of a sterile field, and includes a user control interface including a plurality of parameters. The projector is configured to be in communication with the first medical device, the projector configured to project a mixed reality visual representation of the user control interface including the plurality of parameters of the first medical device on a display screen being visible to a user and located within the sterile field.

In some embodiments, the display screen includes a heads up display screen in communication with the projector.

In some embodiments, the display screen includes one or more buttons configured to control the plurality of parameters, the one or more buttons configured to be coupled to a left side or a right side of the display screen.

In some embodiments, the one or more buttons include a clickable scroll wheel.

In some embodiments, the display screen is sterile or configured to be placed in a sterile bag.

In some embodiments, the projector is outside of the sterile field.

In some embodiments, the projector is inside of the sterile field and is sterile or configured to be placed in a sterile bag.

In some embodiments, the projector is coupled to the first medical device or to a second medical device, the second medical device inside the sterile field or outside of the sterile field.

In some embodiments, the display screen includes a display screen console having an energy source, one or more processors, non-transitory computer readable medium and two or more logic modules.

In some embodiments, the two or more logic modules, when executed by the processor, are configured to perform operations including correlating the statue of the one or more buttons with one or more parameter changes on the user control interface, and transmitting the one or more parameter changes to the projector.

In some embodiments, the projector includes a projector console having an energy source, one or more processors, non-transitory computer readable medium and a plurality of logic modules.

In some embodiments, the plurality of logic modules, when executed by the processor, are configured perform operations including receiving the depiction of the user control interface from the first medical device, projecting the mixed reality visual representation of the user control interface, including any parameter changes on the display screen, receiving the one or more parameter changes from the display screen, and transmitting the one or more parameter changes from the projector to the first medical device.

In some embodiments, the display screen is curved.

In some embodiments, the first medical device includes a laser, and the plurality of parameters include laser pulse energy, laser frequency or laser pulse duration.

Also disclosed is a method of controlling a plurality of parameter changes of a medical device from within a sterile field. The method includes placing a projector, having one or more buttons, in communication with a first medical device, the first medical device having a user control interface with a plurality of parameters, the first medical device being outside of a sterile field. The method further includes placing the projector in the sterile field, projecting a mixed reality visual representation of the user control interface on a surface, and providing one or more parameter changes to the first medical device.

In some embodiments, placing the projector having the one or more buttons in communication with the first medical device includes placing the projector having the one or more buttons configured to control the plurality of parameters, in communication with the first medical device.

In some embodiments, placing the projector in the sterile field includes placing the projector in a sterile bag.

In some embodiments, projecting the mixed reality visual representation of the user control interface on the surface includes projecting the mixed reality visual representation of the user control interface on the surface wherein the surface is visible to a user and includes a floor, a ceiling, a surface of a second medical device, or a sterile drape.

In some embodiments, providing one or more parameter changes to the first medical device include providing one or more parameter changes to the first medical device wherein the first medical device includes a laser and the one or more parameter changes include laser pulse energy, laser frequency or laser pulse duration.

Also disclosed is a method of controlling a plurality of parameter changes of a medical device from within a sterile field including placing a projector in communication with a first medical device, the first medical device having a user control interface with a plurality of parameters, the first medical device being outside of a sterile field. The method further includes placing a display screen having one or more buttons, in communication with the projector, placing the display screen in the sterile field, projecting a mixed reality visual representation of the user control interface on the display screen, and providing one or more parameter changes to the first medical device.

In some embodiments, placing the projector in communication with the first medical device, the first medical device having the user control interface with the plurality of parameters includes placing the projector in communication with the first medical device wherein the first medical device is a laser and the plurality of parameters include laser pulse energy, laser frequency, or laser pulse duration.

In some embodiments, placing the display screen in the sterile field includes placing the display screen in a sterile bag.

In some embodiments, providing one or more parameter changes to the first medical device include the one or more buttons of the display screen being manipulated by the user to provide the one or more parameter changes to the first medical device.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 7 illustrates a flow chart of an exemplary method of controlling a plurality of parameter changes of a medical device from within a sterile field, in accordance with some embodiments.

DESCRIPTION

Figure 1:
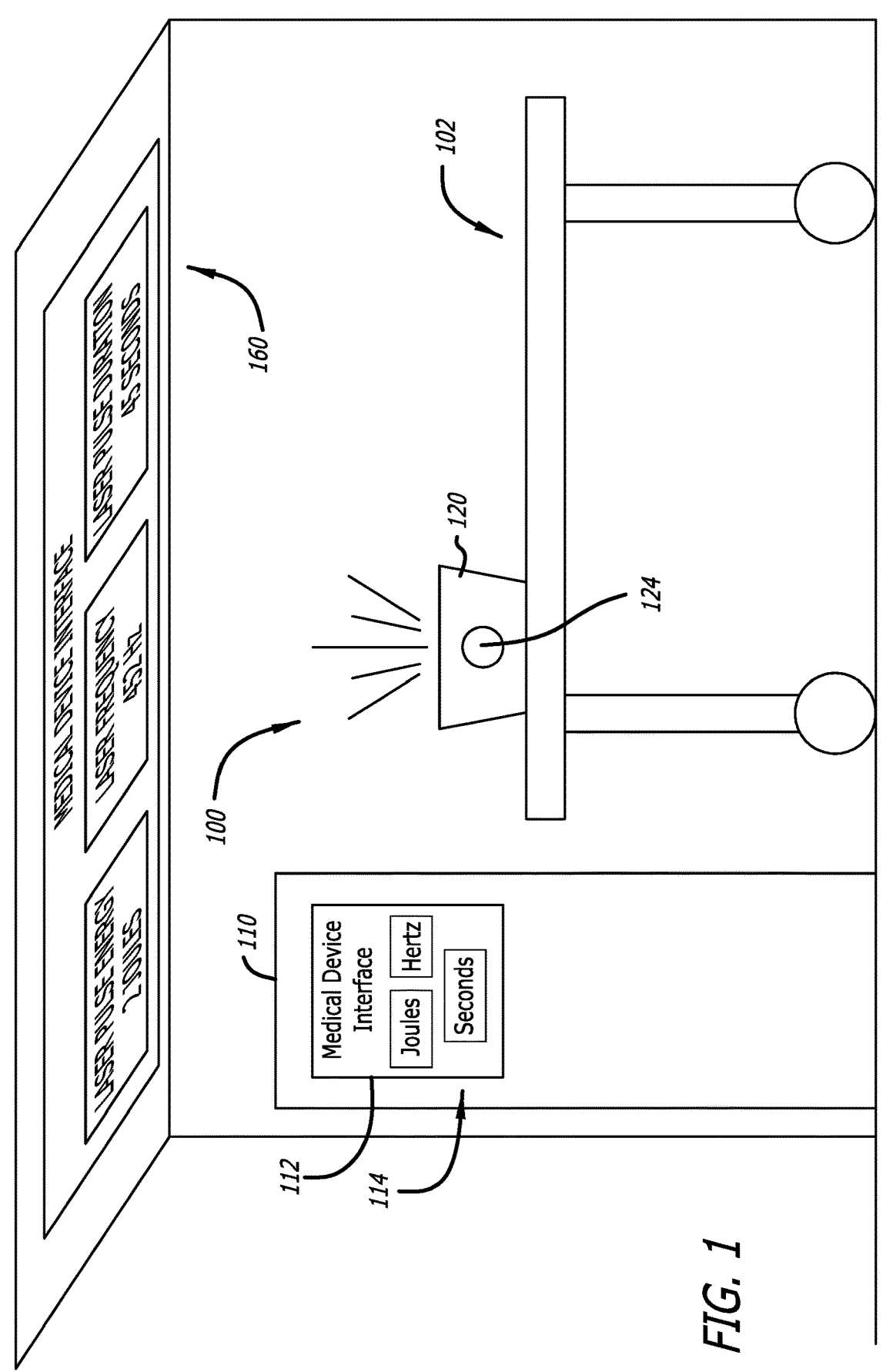
FIG. 1 illustrates a perspective view of a medical device projection system, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semi-conductor memory, or combinatorial elements.

Additionally, or in the alternative, the term logic may refer to or include software such as one or more processes, one or more instances, Application Programming Interface(s) (API), subroutine(s), function(s), applet(s), servlet(s), rou-tine(s), source code, object code, shared library/dynamic link library (dll), or even one or more instructions. This software may be stored in any type of a suitable non-transitory storage medium, or transitory storage medium (e.g., electrical, optical, acoustical or other form of propa-gated signals such as carrier waves, infrared signals, or digital signals). Examples of a non-transitory storage medium may include, but are not limited or restricted to a programmable circuit; non-persistent storage such as vola-tile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

With respect to "alternative reality," the term alternative reality may pertain to virtual reality, augmented reality, and mixed reality unless context suggests otherwise. "Virtual reality" includes virtual content in a virtual setting, which setting can be a fantasy or a real-world simulation. "Aug-mented reality" and "mixed reality" include virtual content in a real-world setting such as a real depiction of a portion of a patient's body including the anatomical element. Aug-mented reality includes the virtual content in the real-world setting, but the virtual content is not necessarily anchored in the real-world setting. For example, the virtual content can be information overlying the real-world setting. The infor-mation can change as the real-world setting changes due to time or environmental conditions in the real-world setting, or the information can change as a result of a consumer of the augmented reality moving through the real-world set-ting; however, the information remains overlying the real-world setting. Mixed reality includes the virtual content anchored in every dimension of the real-world setting. For example, the virtual content can be a virtual object anchored in the real-world setting. The virtual object can change as the real-world setting changes due to time or environmental conditions in the real-world setting, or the virtual object can change to accommodate the perspective of a consumer of the mixed reality as the consumer moves through the real-world setting. The virtual object can also change in accordance with any interactions with the consumer or another real-world or virtual agent. Unless the virtual object is moved to another location in the real-world setting by the consumer of the mixed reality, or some other real world or virtual agent, the virtual object remains anchored in the real-world setting. Mixed reality does not exclude the foregoing information overlying the real-world setting described in reference to augmented reality.

Unless defined otherwise, all technical and scientific terms used herein have the same meaning as commonly understood by those of ordinary skill in the art.

FIG. 1 illustrates a perspective view of a medical device projection system 100, in accordance with some embodi-ments. In some embodiments, the medical device projection system 100 includes a first medical device 110, residing outside a sterile field 102. In some embodiments, the first medical device 110 includes a screen 112, depicting a user control interface 114 including a plurality of parameters of the first medical device 110. In some embodiments, the first medical device 110 includes a laser that may be configured to dissolve a kidney stone. In some embodiments, the plurality of parameters may include laser pulse energy, laser frequency, laser pulse duration, average power, pulse width, or medical device status (e.g., a standby mode, an active mode or the like). The medical device projection system 100 further includes a projector 120 within the sterile field 102, in communication with the first medical device 110. In some embodiments, the projector 120 may be sterile, configured to be sterilized, or placed within a sterile bag. In some embodi-ments, the projector 120 may be sufficiently robust to remain functional following sterilization cycle or constructed from materials that can withstand typical sterilize techniques (e.g., hardened plastics, polymers or the like).

In some embodiments, the projector 120 may be wired to the first medical device 110 or in wireless communication with the first medical device 110. Exemplary wireless com-munication modalities can include WiFi, Bluetooth, Near Field Communications (NFC), cellular Global System for Mobile Communication ("GSM"), electromagnetic (EM), radio frequency (RF), combinations thereof, or the like. In some embodiments, the projector 120 may be configured to project a mixed reality visual representation of the user control interface 114 on a surface 160 visible to the user. The depiction of the user control interface 114 on the surface 160 visible to the user allows the user to visualize the user control interface 114 including the plurality of parameters, confirming desired parameters or the need to change existing parameters, all in real time. In some embodiments, the surface 160 may be within the sterile field 102 or outside of the sterile field 102. In some embodiments, the surface 160 may include a ceiling, a floor, a wall, a surface of a second medical device, a sterile drape or the like.

In some embodiments, the projector 120 may be config-ured to not only project a mixed reality depiction of the user control interface 114 but also control one or more of the plurality of parameters. In some embodiments, the projector 120 may be configured to include one or more buttons 124 configured to control the plurality of parameters of the first medical device 110. In some embodiments, the one or more buttons 124 may be configured to be manipulated by a user. In some embodiments, the one or more buttons 124 may include a directional pad or a clickable scroll wheel config-ured to allow a user to select a parameter using the click function and then change the parameter using the scroll function. Advantageously, the medical device projection system 100 allows the projector 120 to reside within the sterile field 102 while projecting a mixed reality visual representation of the user control interface 114 of the first medical device 110 onto a surface 160 visible to the user and provide parameter changes to the first medical device 110 from within the sterile field 102.

Figure 2A:
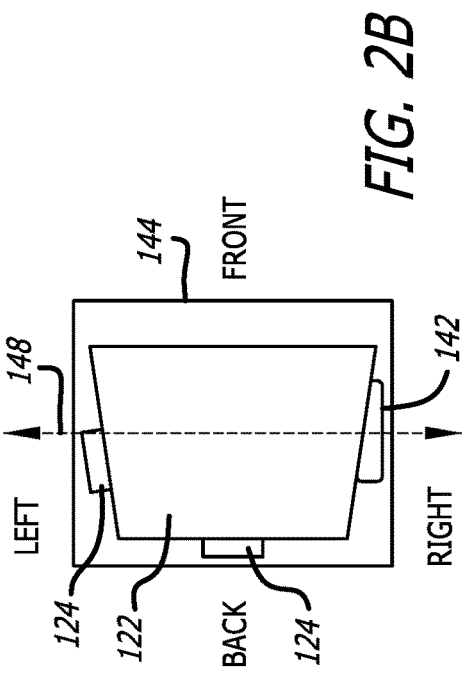
FIG. 2A illustrates a cross sectional side view of a projector of the medical device projection system, in accordance with some embodiments.

FIG. 2A illustrates a cross sectional side view of the projector 120, in accordance with some embodiments. In some embodiments, the projector 120 includes a projector body 122 having a front side and a back side. In some embodiments, the projector body 122 may include the one or more buttons 124 thereon. In some embodiments, the pro-jector body 122 may be coupled to a projector stand 142 configured to stabilize the projector 120 when the projector 120 is within the sterile field 102. In some embodiments, the projector stand 142 may include a projector stand base 144 or two or more projector stand legs. The projector stand 142 may be configured to allow the projector 120 to rotate annularly around a projector stand axis 148, as will be described in more detail herein.

Figure 2B:
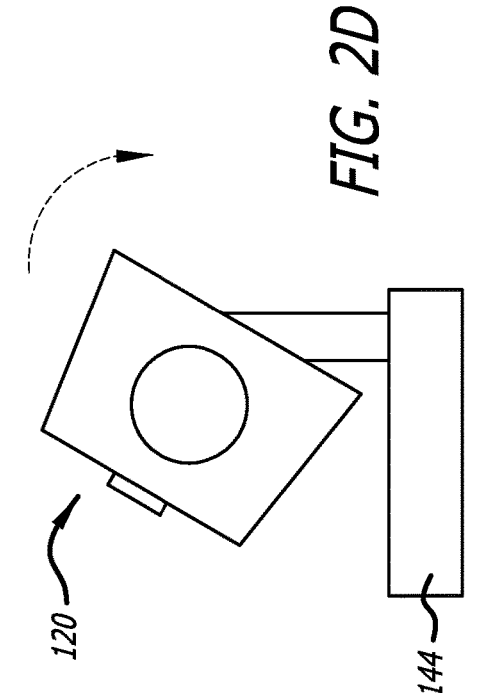
FIG. 2B illustrates a plan view of the projector, in accordance with some embodiments.

FIG. 2B illustrates a plan view of the projector 120, in accordance with some embodiments. The projector body 122 may have a left side or a right side. In some embodiments, the one or more buttons 124 may be coupled to the left side, the right side, the back side, or a combination thereof. In some embodiments, the projector stand 142 may be coupled to the left side or the right side. In some embodiments, the one or more buttons 124 may be coupled to one side and the projector stand 142 may be coupled to the opposite side, allowing the user to adjust projection using the projector stand 142 and adjust the one or more parameters using the one or more buttons 124. In some embodiments, where the projector stand 142 couples to the projector 120 defines the projector stand axis 148.

Figure 2C:
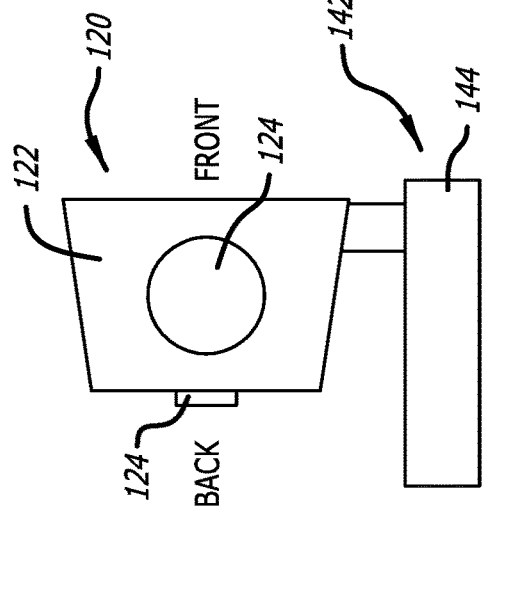
FIGS. 2C-2D illustrate a cross sectional side view of an exemplary method of adjusting the projector to project onto a variety of surfaces, in accordance with some embodiments.
Figure 2D:
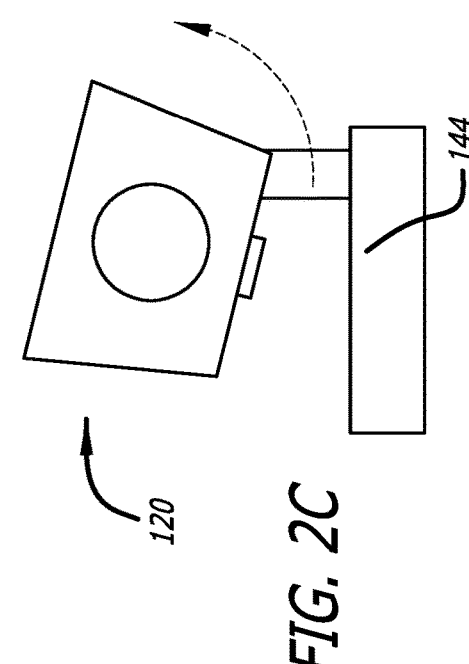

FIGS. 2C-2D illustrate a cross sectional view of an exemplary method of adjusting the projector 120 to project onto a variety of surfaces 160, in accordance with some embodiments. The projector 120 may be rotated around the projector stand axis 148 (see FIG. 2B) to configure the projector 120 to project the mixed reality visual representation of the user control interface 114 on a variety of surfaces 160 (see FIG. 1). In some embodiments, the projector 120 may be rotated upward to be perpendicular to the projector stand base 144. In some embodiments, the projector 120 may rotate upward through an angle of 0-110° in relation to the projector stand base 144 as illustrated in FIG. 2C and may rotate downward through an angle of 0 to −60° in relation to the projector stand base 144 as illustrated in FIG. 2D. Rotating the projector 120 upwards through an angle of 0-110° allows the projector 120 to project on a wall surface or ceiling surface. Rotating the projector 120 downward through an angle of 0 to −60° allows the projector to project on a sterile drape or a surface of a second medical device. Advantageously, having the projector 120 configured to rotate upward or downward to project on a surface 160 allows a user to operate within the sterile field 102 while visualizing or controlling the user control interface 114 from within the sterile field 102.

Figure 3:
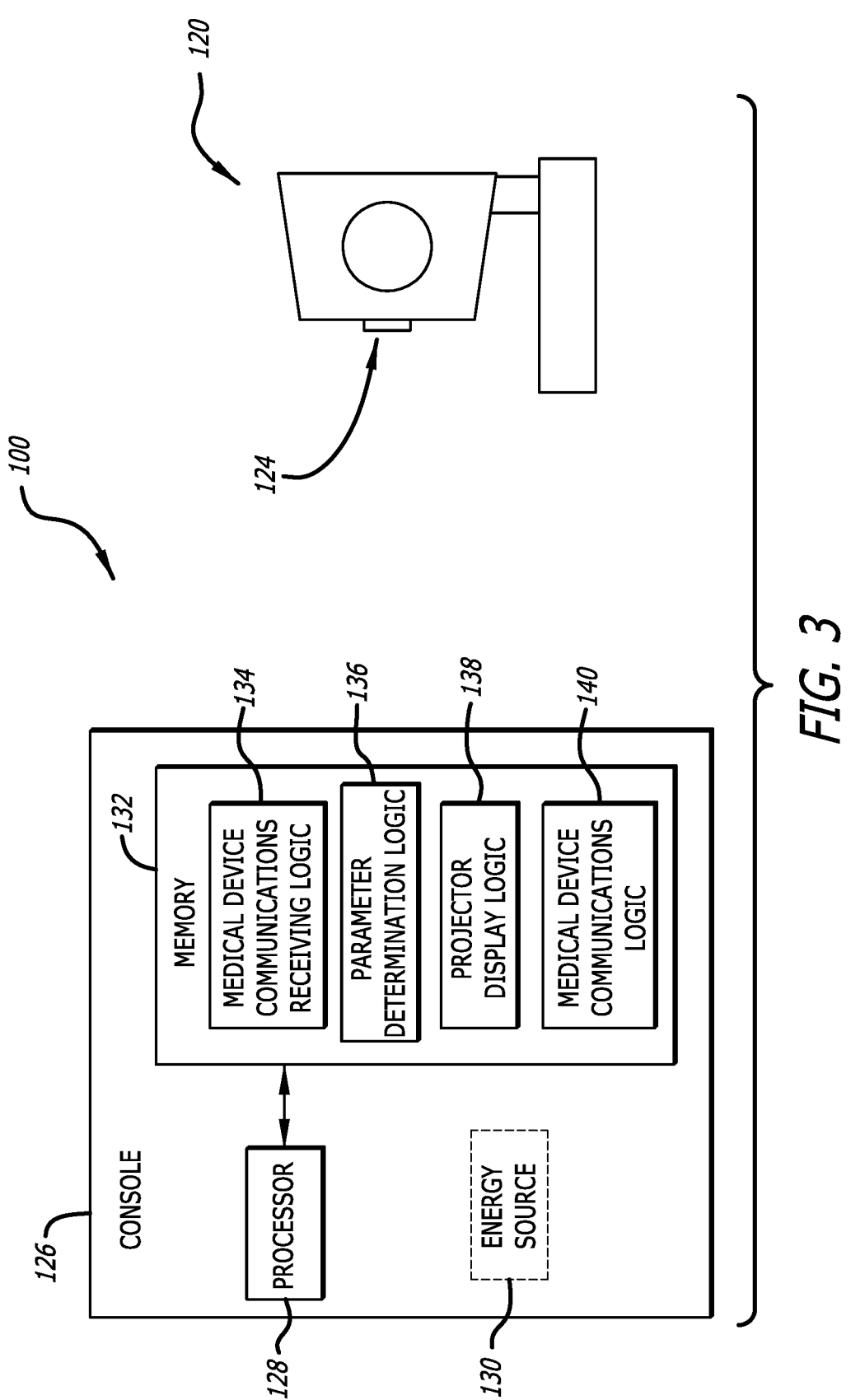
FIG. 3 illustrates a block diagram of some components of the medical device projection system including the projector and a projector console, in accordance with some embodiments.

FIG. 3 illustrates a block diagram of some components of the medical device projection system 100 including a projector console 126, in accordance with some embodiments. In some embodiments, the projector 120 may be configured to include a projector console 126 including one or more processors 128, an energy source 130, non-transitory computer readable medium ("memory") 132 and a plurality of logic modules. In some embodiments, the projector console 126 may be coupled to the projector 120, located within the projector 120, or located within the projector stand 142. In some embodiments, the plurality of logic modules may be configured to include one or more of: a medical device communications receiving logic 134, a parameter determination logic 136, a projector display logic 138, and a medical device communications logic 140. In some embodiments, the medical device communications receiving logic 134 may be configured to receive communications from the first medical device 110 including the depiction of the user control interface 114. In some embodiments, the parameter determination logic 136 may be configured to correlate the status (e.g., physical location, orientation, or the like) of the one or more buttons 124 with one or more parameter changes on the user control interface 114. In some embodiments, the projector display logic 138 may be configured to project the mixed reality depiction of the user control interface 114, including any parameter changes, on the surface 160. In some embodiments, the medical device communications logic 140 may be configured to transmit the one or more parameter changes from the projector 120 to the first medical device 110.

Figure 4:
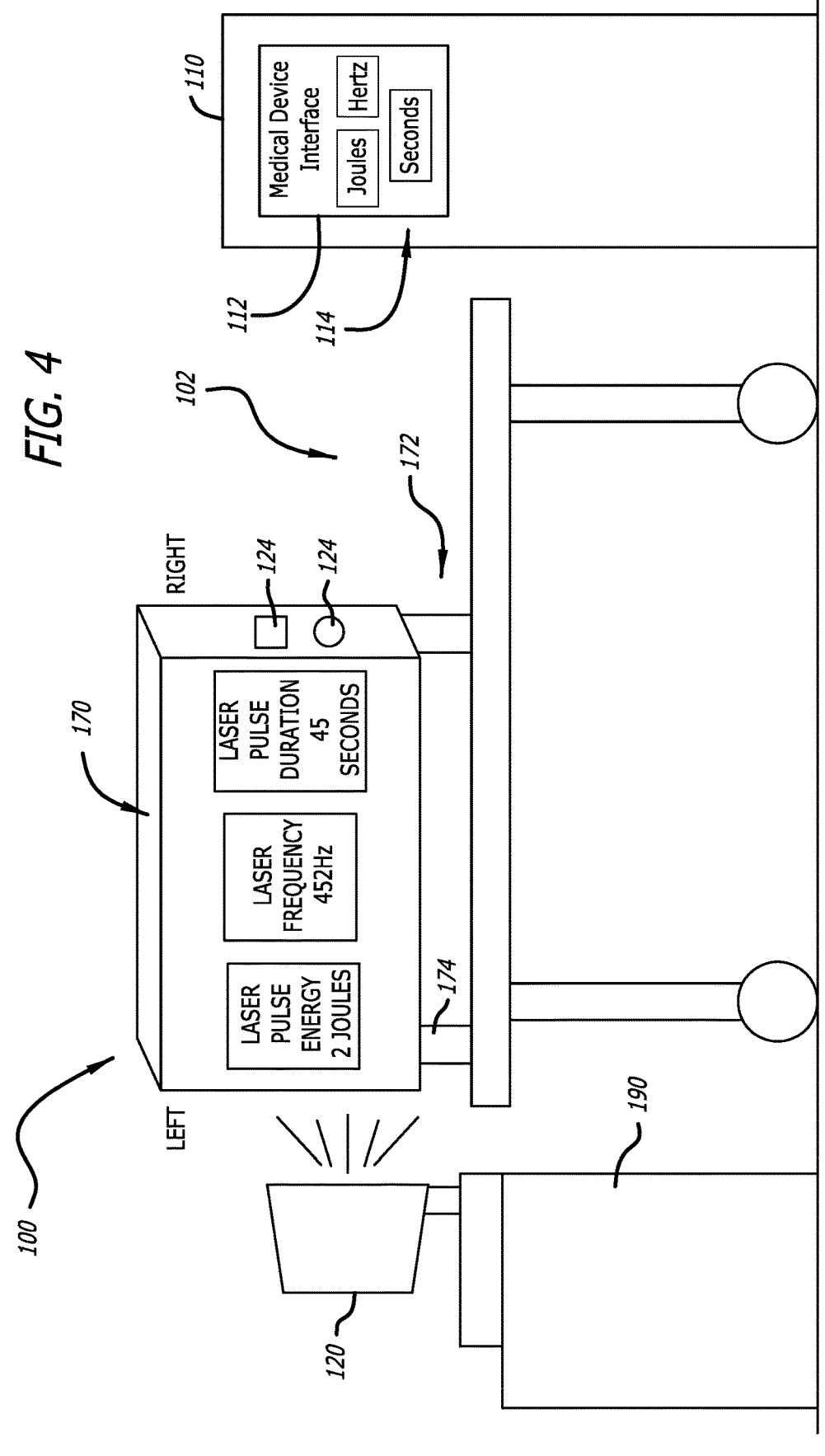
FIG. 4 illustrates a perspective view of the medical device projector system including the projector and a display screen in accordance with some embodiments.

FIG. 4 illustrates a perspective view of the medical device projection system 100, in accordance with some embodiments. In some embodiments, the medical device projection system 100 includes the first medical device 110 as described above. In some embodiments, the medical device projection system 100 includes the projector 120 as described above configured to project a mixed reality visual representation of the user control interface 114 on a display screen 170 that is visible to a user. In some embodiments, the projector 120 may reside outside the sterile field 102 and the display screen 170 may reside within the sterile field 102. In some embodiments, the projector 120 may reside within the sterile field 102. In some embodiments, the display screen 170 may be sterile, configured to be sterilized, or placed within a sterile bag. In some embodiments, the display screen 170 may be sufficiently robust to remain functional following sterilization cycle or constructed from materials that can withstand typical sterilize techniques (e.g., hardened plastics, polymers or the like).

In some embodiments, the projector 120 may be in wireless communication with the display screen 170. Exemplary wireless communication modalities can include WiFi, Bluetooth, Near Field Communications (NFC), cellular Global System for Mobile Communication ("GSM"), electromagnetic (EM), radio frequency (RF), combinations thereof, or the like. In some embodiments, the projector 120 may be configured to display on the display screen 170 a mixed reality visual depiction of the user control interface 114. In some embodiments, the display screen 170 may include a heads up display, allowing the user to see the mixed reality visual representation of the user control interface 114 on the display screen 170, but also see real world objects through the display screen 170 including the patient. In some embodiments, the display screen 170 may be curved to allow for optimal user viewing from all angles. In some embodiments, the display screen 170 may include one or more buttons 124 configured to control parameters on the user control interface 114. In some embodiments, the one or more buttons 124 may be manipulated by a user. In some embodiments, the one or more buttons 124 may be coupled to a right side or a left side of the display screen 170.

In some embodiments, the display screen 170 may include a display screen base 172, having two or more display screen legs 174 configured to stabilize the display screen 170 within the sterile field 102. In some embodiments, the projector 120 may be configured to be coupled to the first medical device 110 or may be coupled to a second medical device 190. In some embodiments, the second medical device 190 may be outside of the sterile field 102 or within the sterile field 102. In an embodiment, the projector 120 may be contained within a dongle configured to be plugged into a computing device or the first medical device 110 or the second medical device. In this embodiment, the computing device, first medical device 110 or the second medical device 190 may be configured to provide an energy source for the projector 120.

Figure 5:
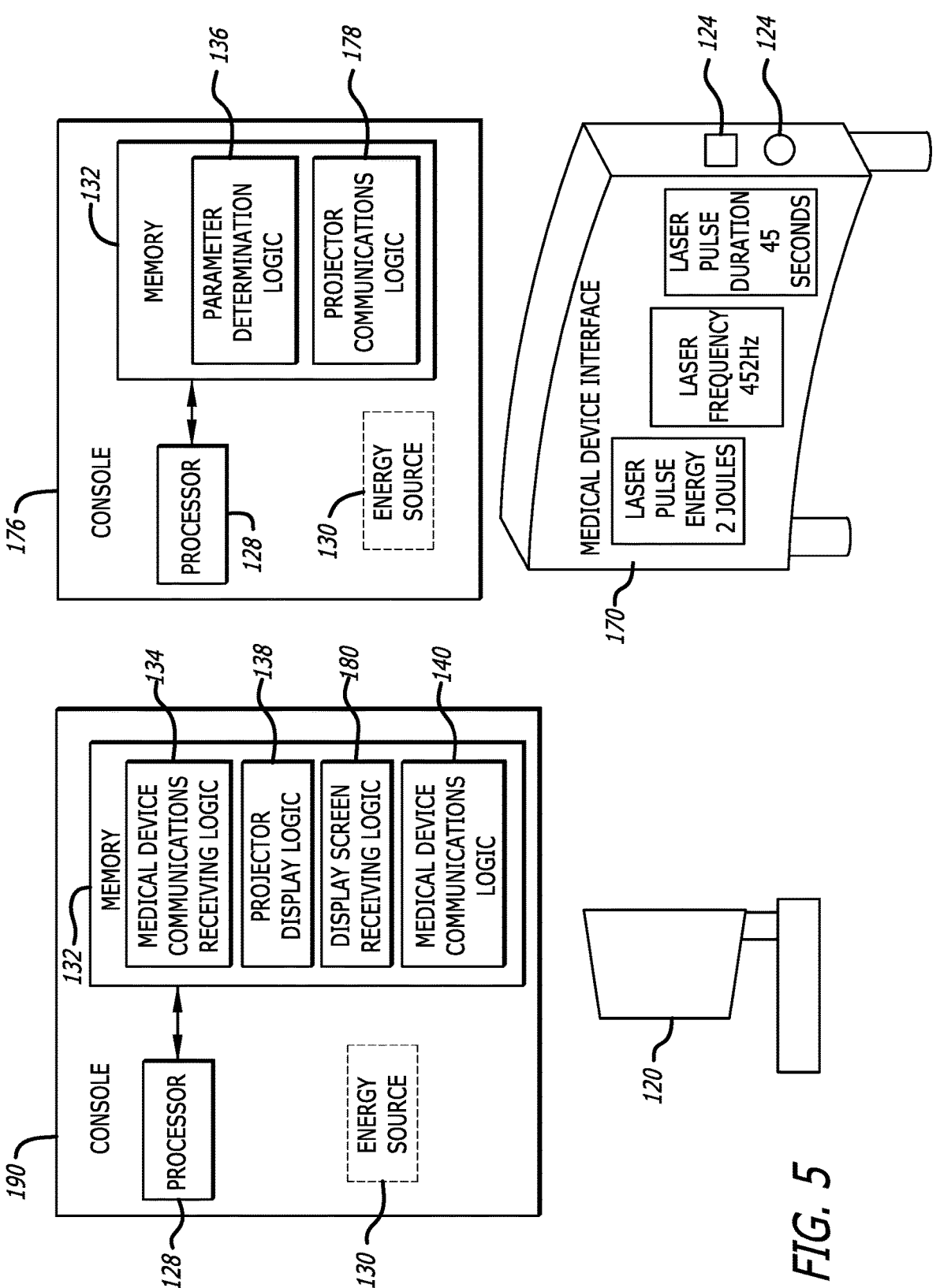
FIG. 5 illustrates a block diagram of some components of the medical device projection system including the projector console, a display screen, and a display screen console, in accordance with some embodiments.

FIG. 5 illustrates a block diagram of some components of the medical device projection system 100 including the projector 120, the projector console 126, and a display screen console 176, in accordance with some embodiments. In some embodiments, the projector 120 may include the projector console 126 and the display screen 170 may include a display screen console 176. In some embodiments, the projector console 126 includes one or more processors 128, a first energy source 130, non-transitory computer readable medium ("memory") 132 and a first plurality of logic modules. In some embodiments, the plurality of logic modules may include one or more of the medical device communications receiving logic 134, the projector display logic 138 and the medical device communications logic 140, as described above.

In some embodiments, the plurality of logic modules may include a display screen receiving logic 180. In some embodiments, the display screen receiving logic 180 may be configured to receiving the one or more parameter changes from the display screen 170. In some embodiments, the display screen console 176 may include one or more processors 128, a second energy source 130, non-transitory computer readable medium ("memory") 132 having two or more logic modules. In some embodiments, the two or more logic modules may include the parameter determination logic 136 or a projector communications logic 178. In some embodiments, the parameter determination logic 136 may be configured to correlate the status of the one or more buttons 124 with one or more parameter changes on the user control interface 114. In some embodiments, the projector communications logic 178 may be configured to transmit the one or more parameter changes to the projector 120.

Figure 6:
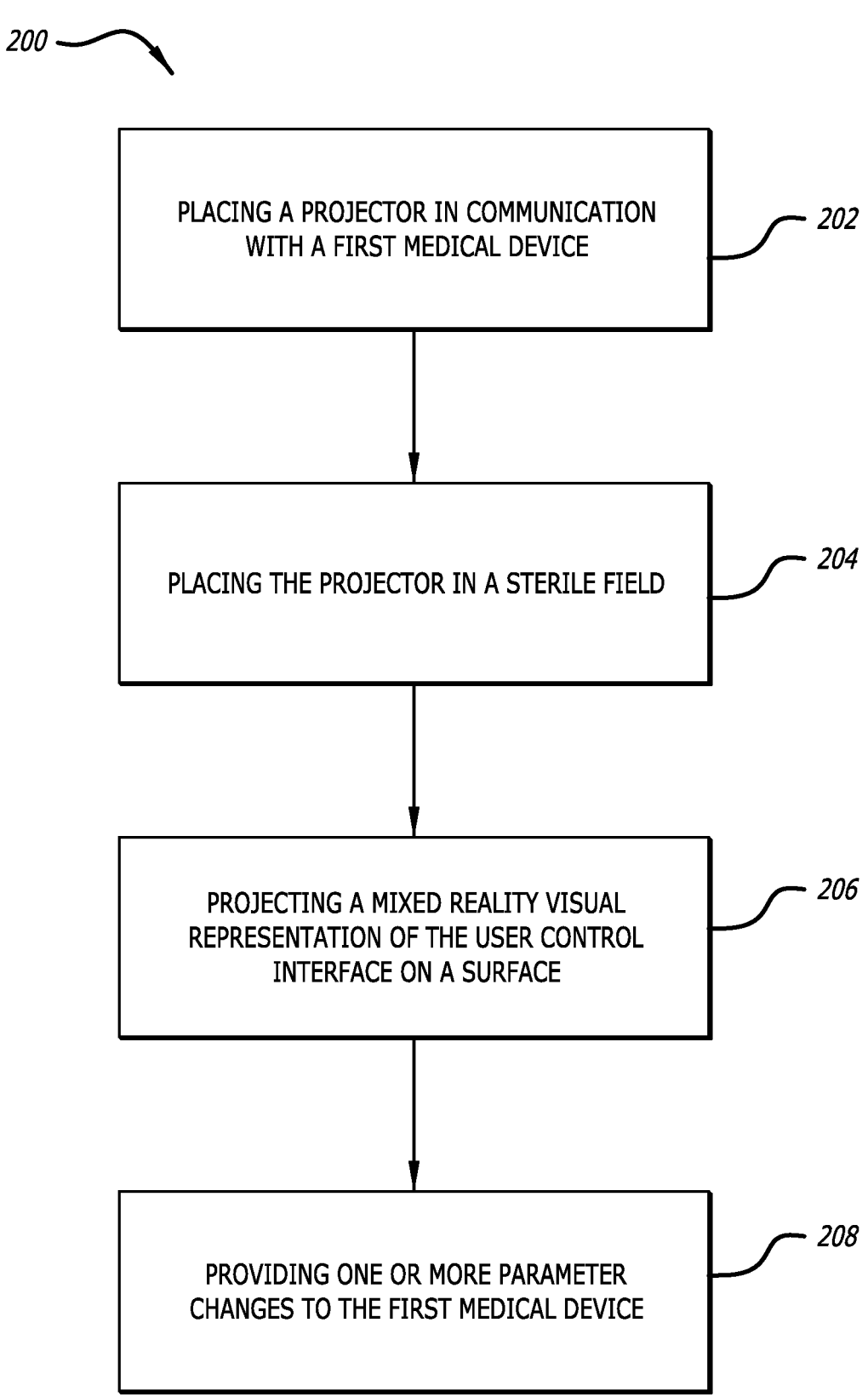
FIG. 6 illustrates a flow chart of an exemplary method of controlling a plurality of parameter changes of a medical device from within a sterile field, in accordance with some embodiments.

FIG. 6 illustrates a flow chart of an exemplary method 200 of controlling a plurality of parameter changes of a first medical device 110 from within the sterile field 102, in accordance with some embodiments. In some embodiments, the method 200 includes placing the projector 120 in communication with the first medical device 110 (block 202). In some embodiments, the first medical device 110 is outside of the sterile field 102 and includes the user control interface 114 having the plurality of parameters. In some embodiments, the projector 120 includes the one or more buttons 124 configured to control the plurality of parameters. In some embodiments, the one or more buttons 124 may include a clickable scroll wheel. In some embodiments, placing the projector 120 in communication with the first medical device 110 includes placing the projector 120 in wireless communication with the first medical device 110.

The method 200 further includes placing the projector 120 in the sterile field 102 (block 204). In some embodiments, the projector 120 is sterile. In some embodiments, placing the projector 120 in the sterile field 102 includes placing the projector 120 in a sterile bag. In some embodiments, the sterile bag is clear. The method 200 further includes projecting a mixed reality visual representation of the user control interface 114 on a surface 160 (block 206). In some embodiments, projecting a mixed reality visual representation of the user control interface 114 includes projecting a mixed reality visual representation of the user control interface 114 as the user provides parameter changes in real time. In some embodiments, the surface 160 is visible to a user. In some embodiments, the surface 160 includes a floor, a ceiling, a surface of a second medical device, a sterile drape or the like.

The method 200 further includes providing one or more parameter changes to the first medical device 110 (block 208). In some embodiments, providing one or more parameter changes to the first medical device 110 includes the one or more buttons 124 being manipulated by the user to provide the one or more parameter changes to the first medical device 110. For example, when the one or more buttons 124 include the clickable scroll wheel, the user may twist the clickable scroll wheel to increase or decrease one or more parameters. In some embodiments, providing one or more parameter changes include the projector 120 transmitting the one or more parameter changes to the first medical device 110. In some embodiments, the first medical device 110 may include a laser. In some embodiments, the plurality of parameters may include laser pulse energy, laser frequency and laser pulse duration.

FIG. 7 illustrates a flow chart of an exemplary method 300 of controlling a plurality of parameter changes of a first medical device 110 from within a sterile field 102, in accordance with some embodiments. The method 300 includes placing the projector 120 in communication with the first medical device 110 of the medical device projection system 100 (block 302). In some embodiments, placing the projector 120 in communication with the first medical device 110 includes placing the projector 120 in wireless communication with the first medical device 110. In some embodiments, placing the projector 120 in communication with the first medical device 110 includes placing the projector 120 in communication with the first medical device 110 having the user control interface 114 with the plurality of parameters. In some embodiments, placing the projector 120 in communication with the first medical device 110 includes placing the projector 120 in communication with the first medical device 110, wherein the first medical device 110 may be outside of the sterile field 102.

The method 300 includes placing the display screen 170 in communication with the projector 120 (block 304). In some embodiments, placing the display screen 170 in communication with the projector 120 includes placing the display screen 170 in wireless communication with the projector 120. In some embodiments, the display screen 170 includes one or more buttons 124 configured to control the plurality of parameters. In some embodiments, the one or more buttons 124 include a clickable scroll wheel. The method 300 further includes placing the display screen 170 in the sterile field 102 (block 306). In some embodiments, the display screen 170 is visible to a user. In some embodiments, the display screen 170 is sterile. In some embodiments, the display screen 170 may be placed in a sterile bag. In some embodiments, the sterile bag is clear. The method 300 further includes projecting a mixed reality visual representation of the user control interface 114 on the display screen 170 (block 308). In some embodiments, projecting a mixed reality visual representation of the user control interface 114 includes projecting a mixed reality visual representation of the user control interface 114 as the user provides parameter changes in real time.

The method 300 further includes providing one or more parameter changes to the first medical device 110 (block 310). In some embodiments, providing one or more parameter changes include the one or more buttons 124 on the display screen 170 being manipulated by the user to provide the changes. For example, when the one or more buttons 124 include the clickable scroll wheel, the user may twist the clickable scroll wheel to increase or decrease one or more parameters. In some embodiments, providing one or more changes include the display screen 170 transmitting the one or more parameter changes to the projector 120 and the projector 120 transmitting the one or more parameter changes to the first medical device 110. In some embodiments, the first medical device 110 may include a laser. In some embodiments, the plurality of parameters may include laser pulse energy, laser frequency and laser pulse duration.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A medical device projection system, comprising:
a first medical device placed outside of a sterile field, wherein the first medical device having includes a screen configured to display a user control interface including a plurality of parameters corresponding to operability of the first medical device; and
a projector placed within the sterile field, wherein the projector is in communication with the first medical device and is configured to project a visual representation of the user control interface on a surface that is outside of the sterile field, and wherein the projector includes one or more buttons configured to control the plurality of parameters, the one or more buttons being coupled to a left side, a right side, or a back side of a projector body.

2. The medical device projection system according to claim 1, wherein the surface is visible to a user.

3. The medical device projection system according to claim 2, wherein the surface includes a floor, a ceiling, a surface of a second medical device, or a sterile drape.

4. The medical device projection system according to claim 1, wherein the one or more buttons include a clickable scroll wheel.

5. The medical device projection system according to claim 1, wherein the projector includes the projector body coupled to a projector stand, the projector stand coupled to the right side or the left side of the projector body.

6. The medical device projection system according to claim 5, wherein the projector stand includes a projector stand base or two or more projector stand legs.

7. The medical device projection system according to claim 5, wherein the projector is configured to rotate annularly around a projector stand axis.

8. The medical device projection system according to claim 1, wherein the projector includes a console having an energy source, one or more processors, non-transitory computer readable medium, one or more buttons, and a plurality of logic modules.

9. The medical device projection system according to claim 8, wherein the plurality of logic modules, when executed by the one or more processors, are configured to perform operations including:
receiving a depiction of the user control interface from the first medical device;
correlating a status of the one or more buttons with one or more parameter changes on the user control interface;
projecting the visual representation of the user control interface, including any parameter changes on the surface; and
transmitting the one or more parameter changes from the projector to the first medical device.

10. The medical device projection system according to claim 1, wherein the first medical device includes a laser and the plurality of parameters include laser pulse energy, laser frequency, and laser pulse duration.

11. The medical device projection system according to claim 1, wherein the projector is configured to be sterile or placed into a sterile bag.

12. A medical device projection system, comprising:
a first medical device placed outside of a sterile field, wherein the first medical device includes a screen configured to display a user control interface including a plurality of parameters corresponding to operability of the first medical device;
a projector placed within the sterile field and in communication with the first medical device, the projector configured to project a visual representation of the user control interface including the plurality of parameters of the first medical device on a display screen; and
the display screen being visible to a user, wherein the display screen includes one or more buttons configured to control the plurality of parameters, the one or more buttons configured to be coupled to a left side or a right side of the display screen.

13. The medical device projection system according to claim 12, wherein the display screen includes a heads up display screen in communication with the projector.

14. The medical device projection system according to claim 12, wherein the one or more buttons include a clickable scroll wheel.

15. The medical device projection system according to claim 12, wherein the display screen is sterile or configured to be placed in a sterile bag.

16. The medical device projection system according to claim 12, wherein the projector is inside of the sterile field and is sterile or configured to be placed in a sterile bag.

17. The medical device projection system according to claim 12, wherein the projector is coupled to the first medical device or to a second medical device, the second medical device inside the sterile field or outside of the sterile field.

18. The medical device projection system according to claim 12, wherein the display screen includes a display screen console having an energy source, one or more processors, a non-transitory computer readable medium, one or more buttons, and two or more logic modules.

19. The medical device projection system according to claim 18, wherein the two or more logic modules, when executed by the one or more processors, are configured to perform operations including:
correlating a status of the one or more buttons with one or more parameter changes on the user control interface; and
transmitting the one or more parameter changes to the projector.

20. The medical device projection system according to claim 12, wherein the projector includes a projector console having an energy source, one or more processors, a non-transitory computer readable medium and a plurality of logic modules.

21. The medical device projection system according to claim 20, wherein the plurality of logic modules, when executed by the one or more processors, are configured perform operations including:
receiving a depiction of the user control interface from the first medical device;
projecting the visual representation of the user control interface, including any parameter changes on the display screen;
receiving one or more parameter changes from the display screen; and
transmitting the one or more parameter changes from the projector to the first medical device.

22. The medical device projection system according to claim 12, wherein the display screen is curved.

23. The medical device projection system according to claim 12, wherein the first medical device includes a laser, and the plurality of parameters include laser pulse energy, laser frequency or laser pulse duration.

24. A medical device projection system, comprising:

a first medical device placed outside of a sterile field, wherein the first medical device includes a screen configured to display a user control interface including a plurality of parameters corresponding to operability of the first medical device;

a projector placed within the sterile field and in communication with the first medical device, the projector configured to project a visual representation of the user control interface including the plurality of parameters of the first medical device on a display screen; and the display screen being visible to a user, wherein the display screen includes a display screen console having an energy source, one or more processors, a non-transitory computer readable medium, one or more buttons, and two or more logic modules.

25. The medical device projection system according to claim 24, wherein the two or more logic modules, when executed by the one or more processors, are configured to perform operations including:

correlating a status of the one or more buttons with one or more parameter changes on the user control interface; and transmitting the one or more parameter changes to the projector.

26. A medical device projection system, comprising:

a first medical device placed outside of a sterile field, wherein the first medical device includes a screen configured to display a user control interface including a plurality of parameters corresponding to operability of the first medical device;

a projector placed within the sterile field and in communication with the first medical device, the projector configured to project a visual representation of the user control interface including the plurality of parameters of the first medical device on a display screen, wherein the projector includes a projector console having an energy source, one or more processors, non-transitory computer readable medium and a plurality of logic modules; and the display screen being visible to a user.

27. The medical device projection system according to claim 26, wherein the plurality of logic modules, when executed by the one or more processors, are configured perform operations including:

receiving a depiction of the user control interface from the first medical device;

projecting the visual representation of the user control interface, including any parameter changes on the display screen;

receiving one or more parameter changes from the display screen; and transmitting the one or more parameter changes from the projector to the first medical device.

*    *    *    *    *